(12) United States Patent
Dinc

(10) Patent No.: US 11,813,369 B2
(45) Date of Patent: Nov. 14, 2023

(54) ULTRAVIOLET AND LASER (RED RADIATION, GREEN RADIATION) RADIATION THERAPY

(71) Applicant: RD GLOBAL ARASTIRMA GELISTIRME SAGLIK ILAC INSAAT YATIRIMLARI SANAYI VE TICARET ANONIM SIRKETI, Ankara (TR)

(72) Inventor: Rasit Dinc, Ankara (TR)

(73) Assignee: RD GLOBAL ARASTIRMA GELISTIRME SAGLIK ILAC INSAAT YATIRIMLARI SANAYI VE TICARET ANONIM SIRKETI, Ankara (TR)

( * ) Notice: Subject to any disclaimer, the term of this patent is extended or adjusted under 35 U.S.C. 154(b) by 544 days.

(21) Appl. No.: 16/886,798

(22) Filed: May 29, 2020

(65) Prior Publication Data

US 2021/0283284 A1    Sep. 16, 2021

(30) Foreign Application Priority Data

Mar. 11, 2020   (TR) ................................. 2020/03735
Apr. 17, 2020   (TR) ................................. 2020/06149

(51) Int. Cl.
| | | |
|---|---|---|
| *A61L 2/10* | (2006.01) | |
| *A61N 5/06* | (2006.01) | |
| *A61N 5/067* | (2006.01) | |

(52) U.S. Cl.
CPC .............. *A61L 2/10* (2013.01); *A61N 5/0624* (2013.01); *A61L 2202/11* (2013.01); *A61L 2202/24* (2013.01); *A61N 5/067* (2021.08)

(58) Field of Classification Search
CPC .... A61L 2/10; A61L 2202/11; A61L 2202/24; A61N 5/0624; A61N 5/067; A61N 2005/0661; A61N 2005/0662
See application file for complete search history.

(56) References Cited

U.S. PATENT DOCUMENTS 6,270,492 B1 *   8/2001  Sinofsky .............. A61N 5/0601
                                                606/7
6,350,041 B1 *   2/2002  Tarsa ...................... F21V 29/74
                                                362/345

(Continued)

*Primary Examiner* — Regina M Yoo
(74) *Attorney, Agent, or Firm* — Bayramoglu Law Offices LLC

(57) ABSTRACT

An ultraviolet radiation and laser radiation (red radiation, green radiation) device or catheter system, a broad spectrum treatment product that affects various pathogens such viral, fungal, bacterial, parasitic causing infections. The ultraviolet radiation and laser radiation device or catheter system is based on the process of eliminating the bacteria, fungi, parasites, and viruses in the body as a result of the ultraviolet light being introduced into the body (intravascular, intrapulmonary, intrarespiratory system, intragastric, intragastrointestinal system, intraarticular, intravesical, intraurogenital system) with the help of a disposable catheter. The ultraviolet radiation and laser radiation device or catheter system is the process of applying the laser and ultraviolet radiations used outside the body directly into the body to the infected tissues and organs with no/minimal damage (not to exceed the toxic limit) to the living creatures.

42 Claims, 3 Drawing Sheets

(56) References Cited

U.S. PATENT DOCUMENTS

| | | | | |
|---|---|---|---|---|
| 6,583,772 | B1* | 6/2003 | Lewis | G02B 27/017 |
| | | | | 359/201.1 |
| 8,744,570 | B2* | 6/2014 | Lee | A61N 5/0622 |
| | | | | 607/54 |
| 2003/0233138 | A1* | 12/2003 | Spooner | A61N 5/0616 |
| | | | | 607/93 |
| 2005/0020926 | A1* | 1/2005 | Wiklof | A61B 1/045 |
| | | | | 348/E9.011 |
| 2005/0116179 | A1* | 6/2005 | Aguirre | F21V 29/80 |
| | | | | 250/492.1 |
| 2005/0116635 | A1* | 6/2005 | Walson | F21K 9/68 |
| | | | | 313/506 |
| 2005/0117366 | A1* | 6/2005 | Simbal | G02B 19/0066 |
| | | | | 362/558 |
| 2005/0276553 | A1* | 12/2005 | Kazakevich | A61B 1/0684 |
| | | | | 385/115 |
| 2010/0222852 | A1* | 9/2010 | Vasily | A61N 5/0616 |
| | | | | 607/88 |
| 2011/0295347 | A1* | 12/2011 | Wells | A61N 5/0622 |
| | | | | 607/89 |
| 2015/0257811 | A1* | 9/2015 | Schwartz | A61N 5/1027 |
| | | | | 606/20 |
| 2020/0151948 | A1* | 5/2020 | Mehedy | A61B 5/444 |

* cited by examiner

ULTRAVIOLET AND LASER (RED RADIATION, GREEN RADIATION) RADIATION THERAPY

CROSS REFERENCES TO THE RELATED APPLICATIONS

This application is based upon and claims priority to Turkish Patent Application No. 2020/03735, filed on Mar. 11, 2020, the entire contents of which are incorporated herein by reference.

TECHNICAL FIELD

The invention relates to ultraviolet radiation and laser (red radiation and green radiation) radiation therapy, a broad spectrum treatment product that affects various pathogens such as viral, fungal, bacterial, and parasitic causing infections.

BACKGROUND

Viral, bacterial, parasitic, and fungal diseases are diseases frequently seen in society. Usually in viral, bacterial, fungal, and parasitic infections, these organisms that settle in the blood and body cavities are tried to be treated with antibiotics, antimycotic, antiparasitic, and antiviral drugs. Ultraviolet radiation therapy is one of the methods generally used in sterilization (non-body usage areas, especially surface sterilization). Ultraviolet radiations are originally radiations coming to the earth through the solar system and Ultraviolet (UV) irradiation is electromagnetic irradiation with a wavelength (100-400 nm) shorter than visible light (400-700 nm) but longer than x-rays (<100 nm). UV irradiation is divided into four separate spectral areas, including vacuum UV (100-200 nm), UVC (200-280 nm), UVB (280-315 nm) and UVA (315-400 nm).

The ultraviolet radiation which is the most effective against bacteria, virus, parasite, and fungal spores, is the UVC radiation. UVC radiations can kill all kinds of microorganisms with their short wavelength and high energy. The greatest anti-microbial activity is in the 250-270 nanometer wavelength region. This wavelength is the wavelength most effectively absorbed by DNA and RNA. Ultraviolet C radiation is an alternative innovative approach to the existing methods used in the treatment of localized infections.

Usage Areas of UV Radiation:
Air Sterilization
Surface Sterilization
Water Sterilization, Water Treatment Systems
Disinfection of Instruments and Equipment
Disinfection of Food Packaging
Usage in the ventilation system of tuberculosis patients
Usage of UVC in odor control has many application fields, including wastewater facilities, farms, commercial kitchens (HVAC) and food processing facilities.
It is also critical for purifying air in industries such as UVC germicidal lamps, printing, plastic, and rubber, where harmful and toxic chemicals are produced.
Disinfection of air and surfaces of operating rooms, clean room laboratories, and biological safety cabinets, in the inhibition of microorganisms in the air in the production area with UVC light applications
It has the potential to significantly reduce hepatitis C virus (HCV) infections of blood products.
Treatment of jaundice disease in infants in newborn units
It is frequently used in sterilization of blood and plasma products.

Contrary to what is known, selected with appropriate doses, UVC can selectively inactivate microorganisms while maintaining the viability of mammalian cells, and it has also been proven that UVC promotes wound healing. UVC (200 nm-280 nm) has been proven to cause less damage to tissue than UVB in animal studies. Although UVC can cause DNA damage in mammalian cells, DNA can be quickly repaired by the repair enzymes. Briefly, UVC is an innovative treatment method of our age as an alternative approach to existing methods that are used for the treatment of localized infections, especially diseases caused by antibiotic-resistant microorganisms, in single-stranded RNA, and double-stranded DNA viruses. UVC should be used in such a way that side effects are minimized and the resistance of microorganisms to UVC is prevented.

Lasers Used in Medicine:
a. Argon Laser: It is used in ophthalmology, it is used in soft tissue approximation and to provide hemostasis, to control bleeding seen in eye ground vein damage and to treat glaucoma (eye pressure).
b. Helium-Neon Laser 632.8 nm Red/Orange: 633 nm does not cause a thermal effect on the tissue. It is used to relieve pain, to reduce inflammation and edema in tissue regeneration.
c. Diode laser 810-980 nm/infrared: Cardiovascular Surgery: Laser treatment for varicosis in the leg venous blood vessels Skin and Plastic Surgery: It is frequently used in areas such as removal of congenital spots, some types of moles, capillaries, and wrinkles that are seen on the skin. It is also used in the removal of tattoos and in some types of skin cancers. Lasers used for anesthesia are also included in this group.

d. Indigo Laser 800-850 nm/infrared: It is used in urological tumors, in the destruction of genital warts, in fracture of renal calculi, in the treatment of enlarged prostate.
e. Neodymium YAG Laser 1064 nm/infrared: It is used in the treatment of brain and spinal cord tumors, tumors obstructing the large intestine in the digestive system, adrenal tumors, fibroids obstructing the tubes in gynecological diseases, tumors of the urinary tract, It is used in stent restenosis such as bypass or angioplasty (balloon opening), treatment of complex lesions, thrombus and extraction of a permanent pacemaker electrode.

f. Thulium Laser 2100 nm/infrared: It is used in the treatment of prostate resection, partial nephrectomy and ureteral strictures in urology.
g. Erbium YAG Laser 2940 nm/infrared: It is preferred for caries cleaning and dental preparation. Today, it has also been put into practice in endodontics and surgery.
h. CO2 Laser 10600 nm/infrared: Bronchoscopes are also frequently used in recent years as they provide both a good field of vision and hemostasis when necessary. It is used in microsurgery and superficial applications.

Laser use is a common practice in medicine. Studies including UVC in the state of the art comprise autoimmune diseases HIV 1-2, T-lymphotropic virus types 1 and 2, Hepatitis B (HBV), Hepatitis C (HCV), Hepatitis A and E, Blood pathogens (*Treponema pallidum*), Parvovirus B19 diseases. However, in these diseases, the blood and organs of the patient are separated from the patient and the pathogens in the blood are destroyed with a UV lamp. In this technique, in order to destroy microorganisms, the patient's blood is taken from the patient, sterilized outside and reintroduced to the patient direct application is not in question. For this reason, this method is not widely used.

In the study conducted by Harald Mohr et al., practice was carried out to reduce the amount of pathogen by UVC application and preparation procedures of existing blood platelets. Platelet samples were irradiated with UV light at 254 nm wavelength in plastic bags (transparent) made of polyolefin acetate, and the total UVC doses applied were adjusted by irradiation time. An irradiation time of 1 minute was applied at approximately 0.4 J/cm2 on both sides and the results were evaluated by two-dimensional gel electrophoresis. With gram-positive (*B. cereus, S. aureus* and *S. epidermidis*) and Gram-negative bacteria (*E. coli, K. Pneumoniae, P. Aeruginosa*) bacterial inactivation with UVC treatment, dosing at 0.4 J/cm2 with 5 log titer reduction, this dose was found equally effective for the following. Again in this method, blood was taken out of the patient, exposed to ultraviolet, and the blood that was re-sterilized was transferred to the patient. Although it is a successful operation, it is not widely used because the blood of the patient is taken out and transferred to the patient again and this process may cause another disease.

The mechanism of UVC inactivation of microorganisms is to damage the genetic material in the nucleus of the cell or nucleic acids in the virus. The UVC spectrum, especially the 250-270 nm range, is strongly absorbed by the nucleic acids of a microorganism and is, therefore, the most lethal wavelength range for microorganisms. The wavelength of 254 nm is known as the germicidal spectrum.

The UVC System uses 254 nm wavelength irradiation that is not absorbed by proteins, so conventional toxicity tests are not required. The method is significantly effective clinically for both gram (+) and gram (−) bacteria, as well as viruses and protozoa. Clinical studies have shown that recovery of UVC irradiated platelets has reduced recovery and shorter survival in the recipient's organism.

Light-induced damage to the DNA and RNA of a microorganism often results from the dimerization of pyrimidine molecules. In particular, thymine (found only in DNA) produces cyclobutane dimers. When thymine molecules are affected by UV and dimerized, it becomes difficult for nucleic acids to multiply and replication often produces a defect that prevents the viability of the microorganism.

UV Properties:

UV 254 nm UV-C radiation:

It is a well-known and essential antimicrobial agent.

It produces non-lethal pathogen damage to stop proliferation and increases susceptibility to immune system disruption.

450 nm Blue Laser radiation:

It regulates our biological rhythms.

It regulates the hormone balance.

It increases the absorption of vitamins.

It regulates the release of serotonin and cortisol.

535 nm Green Laser radiation:

It improves the behavior and functions of red blood cells.

By increasing the flexibility of red blood cells, it provides more oxygen to the tissues.

It improves hemodynamics with reduced blood viscosity.

It enables restorative and balancing paths.

630 nm Red Laser radiation:

It increases the cellular energy level. (ATP Synthesis)

It reduces the production of proinflammatory cytokines.

It regulates immune cell functions, slows down or stops the infection.

In another study, the use of 254 nm UVC light was investigated for the treatment of *Candida albicans* infection in 3rd degree burns in mice. *C. albicans* is the most common fungal pathogen responsible for fungal infection in burn patients and is the fourth most common organism found in blood cultures in intensive care unit patients. As a result of testing UVC on mouse skin, no serious damage was observed in the skin tissue and it was concluded that there was an increase in fungal luminescence loss. It has been concluded that UVC light therapy is effective on mice with this infection.

Although the radiations of UVC and other wavelengths are known in the prior art for killing microorganisms, there is a need for improving the effective use of these techniques on living things and for the treatment of bacterial and viral infections, especially in mammals. Contrary to these external treatments on the skin surface and blood, the invention allows the use of intrarespiratory, intravascular, intragastric, intra-gastrointestinal system, intraarticular, intravesical, intra-urogenital system within the body, thereby eliminating microorganisms.

SUMMARY

The invention is based on the principle of killing microorganisms by applying ultra violet (UVA-UVB-UVC), red laser, blue laser and green lasers within the body. The invention may be a device containing said radiations, used with a catheter/cannula, or a catheter system containing said radiations, which can be used independently of the device.

It allows the selection of the wavelength to be applied by controlling the interface on the device. It works with UV radiation/laser application at the calculated dose, by direct delivery to the intrarespiratory, intravascular, intragastric, intragastrointestinal system, intraarticular, intravesical, intraurogenital system and body cavities through a fiberoptic catheter. UVC and laser light sources and fiber optic cables with connectors are placed on a disposable camera/non-camera catheter. A combination of UVC radiation and laser radiation is used to increase the effectiveness of the treatment.

The invention, unlike the prior art, delivers ultraviolet radiations to the infected area within the body by means of a reflective/fiberoptic lines and a catheter with a normal catheter or isotonic solution, and destroys the microorganisms in these areas. Also, unlike the previous technique, with UV (UVA-UVB-UVC) radiations, with the combined use of laser radiations that support the immune system (immune system), it offers an integrative treatment option.

This process applied with the device/catheter system applied, is the process of applying to the tissues and organs directly infected into the body, with minimal damage (not to exceed the toxic limit), without harming living things (humans, mammals, etc.) by interventional means. The combined radiations used in the invention are an innovative alternative to the existing methods used in the treatment of localized infections. Unlike the existing methods used in medicine, viral, bacterial, parasitic and fungal diseases can be effectively and controllably eliminated by the system allowing direct in-body applications without harming the living creatures.

In contrast to the current uses of UVC, the invention provides UVC and laser radiation application in combination with body cavities while performing direct application via fiberoptic cables or catheter containing solution. In this way, the invention innovates the existing uses of UVC and allows the treatment of different areas within the body. Thus, microorganisms in the body are destroyed within seconds with the anti-inflammatory mechanism of action.

Considering the difficulties in the treatment of diseases caused by microorganisms such as viruses, bacteria, the inventive therapy device/catheter system, which develops with UVC and other radiations, disrupts the connective structure of the bacteria, fungi, parasites and viruses by affecting the nucleic acids in the DNA and RNA chains and inactivates the pathogens that cause infection. It is an innovative alternative approach to existing methods used in the treatment of diseases caused by microorganisms that have developed resistance against active drugs in the body. With these aspects thereof, the invention meets the need to effectively use UVC and other wavelength radiations on living creatures to eliminate viral, bacterial, parasitic and fungal diseases.

Figure 1A:
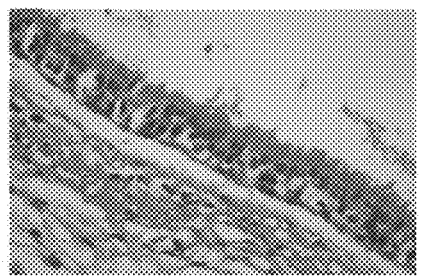
FIG. 1A: UV application for Trachea and Pulmonary Artery before Trachea UV.
Figure 1B:
FIG. 1B: UV application for Trachea and Pulmonary Artery before Pulmonary Artery UV.
Figure 1C:
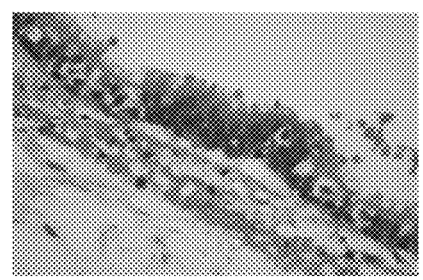
FIG. 1C: UV application for Trachea and Pulmonary Artery after Trachea UV.
Figure 1D:
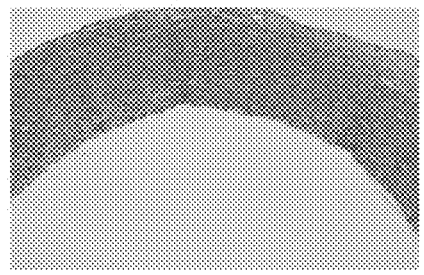
FIG. 1D: UV application for Trachea and Pulmonary Artery after Pulmonary Artery UV.

1: Aluminum casing
2: Aluminum front cover
3: Aluminum rear cover
4: Lower table
5: Relay card
6: Microcontroller card
7: AC/DC power supply
8: DC/DC voltage converter
9: 7" TFT touch screen
10: UVC fluorescent lamp
11: Reflective plate
12: Electronic ballast
13: AC EMI filter
14: 24 V fan
15: Fan protection grid
16: Fiber optic probe/line
17: 660 nm LED (Red)
18: 395 nm LED (Blue)
19: 530 nm LED (Green)
20: Female mold
21: Male mold
22: 220V plug
23: Switch
24: Green power LED

DETAILED DESCRIPTION

The invention is based on the principle of killing microorganisms by applying ultraviolet (UVA-UVB-UVC), red laser, blue laser and green lasers within the body. The invention, which may consist of device and special catheter system, may be a device containing said radiations, used with a catheter/cannula, or a catheter system containing said radiations, which can be used independently of the device.

The radiation device, which is an embodiment of the invention comprises;

3. A device comprising said radiation sources being at least one ultraviolet (UVA-UVB-UVC) (10), at least one 660 red laser (17), at least one 395 nm blue laser (18) and at least one 530 nm green laser (19) LED 4. Fiber optic lines connected to each radiation source (16).

Since the device is applied together with the catheter or cannula configured to fit the fiberoptic lines, the device described above also includes the catheter or cannula.

The fiber optic cables connected to the device/radiation sources of the invention are placed in the Invamed Steerable Catheter (disposable camera catheter) for imaging purposes, or in the normal catheter where there is no camera catheter system. The material of the catheter used in the invention may be pebax (polyether block amide or PEBA), polyamide, polyethylene, metal, Fluorinated ethylene propylene (FEP), Polychlorotrifluoroethylene (PCTFE) or Teflon.

Figure 2:
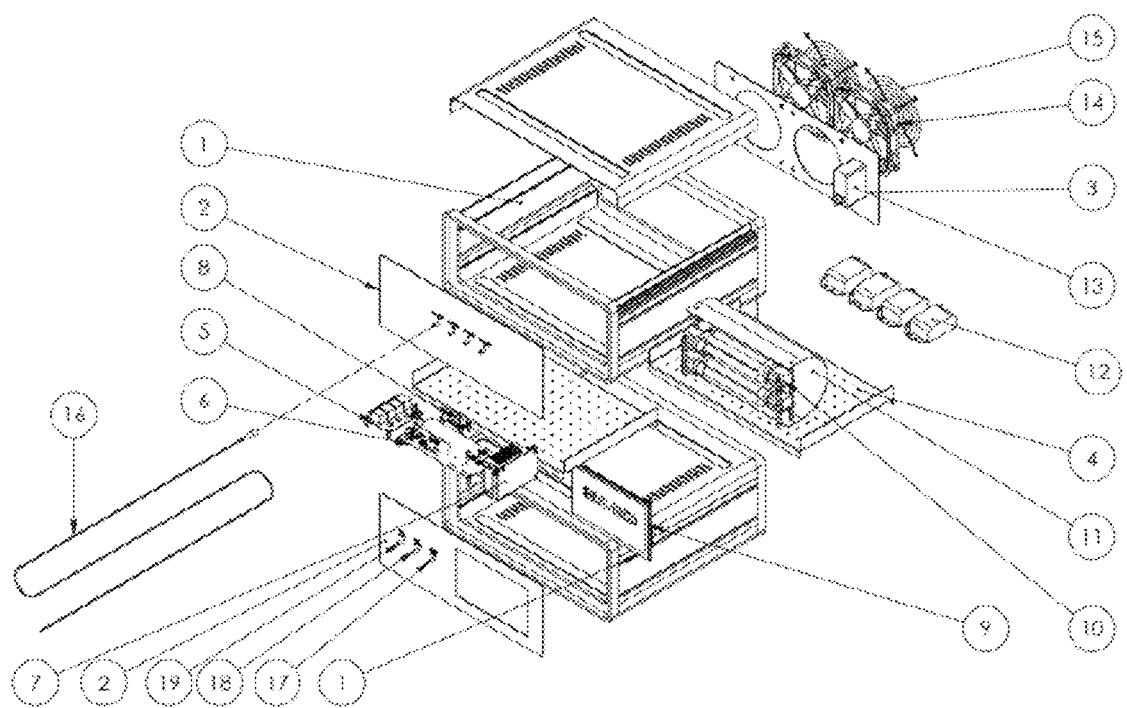
FIG. 2: device of the invention.

Radiation device of the invention comprises:

At least two Aluminum casings (1), Aluminum front cover (2), Aluminum rear cover (3), Lower table (4), 24V fan (14), Fan protection grid (15);

At least one Relay card (5), Microcontroller card (6), AC/DC power supply (7), DC/DC voltage converter (8), 7" TFT touch screen (9), UVC fluorescent lamp (10) (preferably 4 pieces), Reflective plate (11), Electronic ballast (12) (preferably 4 pieces), AC EMI filter (13), Fiber optic probe (16) (preferably 7 pieces), 660 nm LED (17), 395 nm LED (18), 530 nm LED (19) (FIG. 2).

The device of the invention has preferably 4 sources with a wavelength of 254 nm in its UV LED source, allowing for versatile—simultaneous use. In addition to the UV LED source, the device has LEDs with wavelengths of 660 nm laser (red), 395 nm laser (blue), 530 nm laser (green) and the light source created by all these LEDs allows intra-body simultaneous use again through fiber-optic lines. It allows the selection of the wavelength to be applied by controlling over the interface on the device.

UV (UVA-UVB-UVC) (10), 660 nm (17), 395 nm (18) and 530 nm (19) wavelength monochromatic radiations emitted from the end of the fiber optic system destroy microorganisms (including viruses) at the end of an application that takes seconds. Fiberoptic lines that allow UVC and other radiations to be transported and show activity at the target point in the body are compatible with equipment such as catheters and cannula, and can be easily advanced and applied in body cavities, intravascular system. It also allows use with the help of laryngoscope, bronchoscope, endoscopy, colonoscopy, or arthroscopy.

Figure 3:
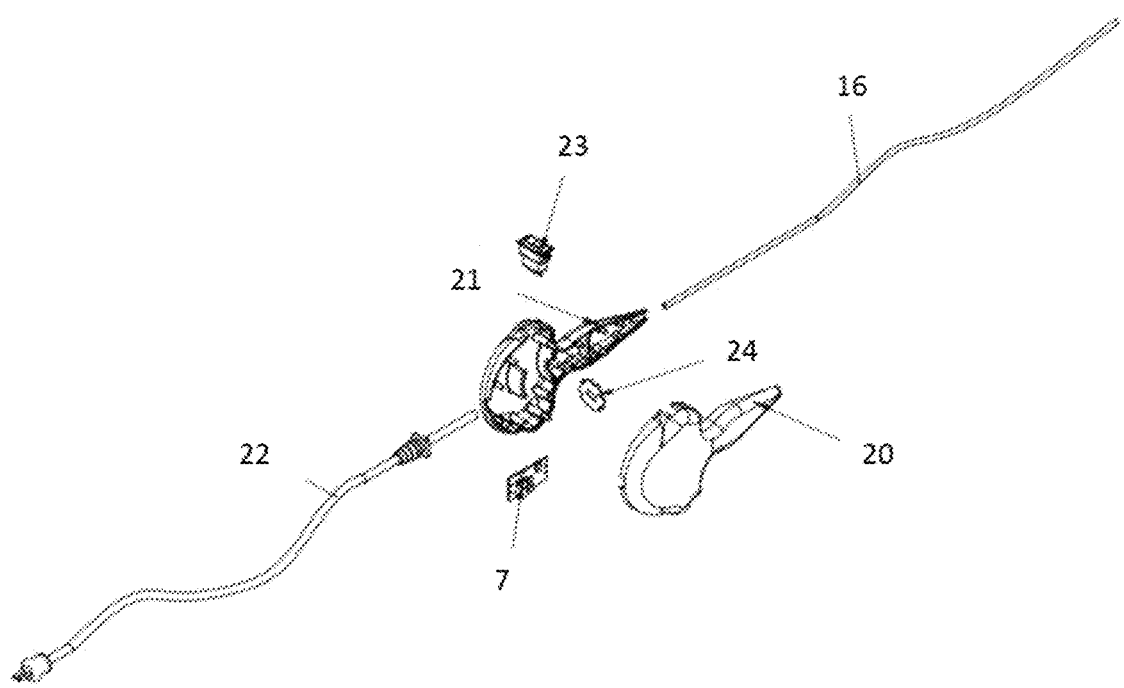
FIG. 3: Disposable catheter system of the invention The elements/parts in the device and disposable catheter system are numbered separately and their explanations are given below.

Disposable catheter system, which is the second application of the invention, includes ultraviolet (UVA-UVB-UVC), red laser, blue laser and green laser LEDs and isotonic solution. Said solution in the content of the catheter is prepared outside before the application and is introduced into the catheter to ensure the transmission of the radiations during the application. The solution is a solution of salts that provides isotonic properties. The ends of the catheter containing the solution are closed in such a way that the solution remains inside, and an optical window is provided to transmit the radiations at the closed end entering the body. Said catheter system comprises:

At least one AC/DC power supply (7), Female mold (20), Male mold (21), 220V plug (22), Switch (23), Green power LED (24) and Fiber-optic probe/line (16) (FIG. 3).

The second embodiment of the invention also allows treatment with the use of a disposable catheter system (FIG.

3) when fiberoptic lines are not used. The disposable catheter system, just like the device in the first embodiment of the invention, includes UV (UVA, UVB, UVC) LED and 660 nm laser (red), 395 nm laser (blue), 530 nm laser (green) sources, thus it operates with UV radiation/laser application at the calculated dose, by sending directly to the intrarespiratory, intravascular, intragastric, intragastrointestinal system, intraarticular, intravesical, intraurogenital system and body cavities.

The invention, which may consist of a device or a disposable catheter system, provides access to the respiratory system with the help of a laryngoscope or a bronchoscope, allowing the infection agents to be cleaned with the same procedure. In the intragastric and intragastrointestinal system applications, it allows the same procedure to be applied by entering with the help of endoscopy or colonoscopy. In intraarticular interventions, the same procedure is applied by performing intra-articular access with the help of arthroscopy. In the genitourinary system, the same procedure is applied by entering with endoscopic applications.

The invention works with the calculated dose of UV light/laser application through the catheter in which the device and fiber-optic lines are placed, or by sending directly to the intrarespiratory, intravascular, intragastric, intragastrointestinal system, intraarticular, intravesical, intraurogenital system and body cavities directly in the disposable catheter system without the device. In this way, the effectiveness of pathogens active in the body is reduced. In intravascular applications, application is carried out for 25-35 minutes.

The important point in the device or catheter system of the invention, is to provide selective inactivation by targeting the host-pathogen without irreversible damage to the cellular DNA of the applied UV dose, with direct intra-body application. It irreversibly destroys the ultrastructural properties of microorganisms while preserving the viability of mammalian cells. As it is stated in FIG. 1, it has been observed that it does not destroy living tissues after application.

In the calculation of the power of ultraviolet (UV), the following formula is taken as the basis and applied to the regions to be applied in the treatment dose and periods specified in the tables (Table 1-5):

UV dose [Joule/m2]=UV radiation intensity [Watt/m2]×Contact duration (seconds)

TABLE 1

| a. Respiratory Application Diameter Mm diameter (mm) | b. Power Per Unit Area mw/cm2 | c. Application Duration sec | d. Energy Required mj/cm² |
|---|---|---|---|
| 5 | 10.00 | 3.60 | 36 |
| 10 | 9.00 | 4.00 | 36 |
| 15 | 8.50 | 4.24 | 36 |
| 20 | 8.10 | 4.44 | 36 |
| 25 | 7.70 | 4.68 | 36 |
| 30 | 7.30 | 4.93 | 36 |
| 35 | 6.90 | 5.22 | 36 |
| 40 | 6.50 | 5.54 | 36 |
| 45 | 6.20 | 5.81 | 36 |
| 50 | 6.00 | 6.00 | 36 |

Application durations are expressed according to the diameters stated in Table-1. a. expresses vessel diameter to be applied; b. expresses the amount of power that reaches the vessel wall of the power coming out of the distal of the fiber/catheter (will change as it moves away from the center); c. expresses calculated application time; d. expresses the amount of energy (mj/cm2) required to sterilize the 1 cm2 area.

TABLE 2

| Application Area | Volume (ml) | Sizes (cm) | a. Area (cm2) | b. Duration required (min) | c. Dosage applied (mJ/cm2) |
|---|---|---|---|---|---|
| Stomach | 1000-1500 ml | 34 × 19 × 18 cm ± %5 | 3200 | 58.14 | 120 |

According to the formula of Table-2; a. Area to be applied; b. the time applied to sterilize; c. energy applied (calculation of the time needed by dividing the applied energy dose per unit area) are shown.

TABLE 3

| Application Area | Size (cm) | Diameter (cm) | a. Area (cm2) | b. Duration required (min) | c. Dosage applied (mJ/cm2) |
|---|---|---|---|---|---|
| Colon | 200 | 7 | 4396 | 43.96 | 36 |
| Jejunum | 250 | 3.5 | 2747.5 | 27.48 | 36 |
| Ileum | 400 | 4 | 5024 | 50.24 | 36 |
| Duodenum | 30 | 2 | 188.4 | 1.88 | 36 |

According to the formula of Table-3; a. Area to be applied; b. the time applied to sterilize; c. energy applied (calculation of the time needed by dividing the applied energy dose per unit area) are shown.

TABLE 4

| Application Area | Sizes (cm) | a. Area (cm2) | b. Duration required (min) | c. Dosage applied (mJ/cm2) |
|---|---|---|---|---|
| Bladder | 10 * 10 * 6 | 520 | 2.25 | 36 |
| Knee | 15 * 15 | 450 | 3.00 | 36 |

According to the formula of Table-4; a. Area to be applied; b. the time applied to sterilize; c. energy applied (calculation of the time needed by dividing the applied energy dose per unit area) are shown.

What is claimed is:

1. A radiation device comprising:
   a plurality of radiation sources comprising at least one ultraviolet source selected from UVA, UVB or UVC, at least one red laser LED with a wavelength of 660 nm, at least one blue laser LED with a wavelength of 395 nm and at least one green laser LED with a wavelength of 530 nm, and
   at least four fiber-optic lines, individually connected to each radiation source of the plurality of radiation sources.

2. The radiation device according to claim 1, comprising a catheter or a cannula configured to accommodate the at least four fiber-optic lines.

3. The radiation device according to claim 2, wherein the catheter is provided with or without a camera.

4. The radiation device according to claim 2, wherein a material of the catheter is polyether block amide, polyamide, polyethylene, metal, FEP, PCTFE or Teflon.

5. The radiation device according to claim 1, wherein the radiation device is configured to apply radiation output from at least a portion of the plurality of radiation sources to an intravascular system, an intrapulmonary system, an intrarespiratory system, an intragastric system, an intragastrointestinal system, an intraarticular system, an intravesical system, or an intraurogenital system.

6. An operation method of the radiation device of claim 1, wherein 36 $mJ/cm^2$ or 120 $mJ/cm^2$ energy is applied to an application area with the radiation device.

7. The operation method according to claim 6, wherein an application energy is 36 $mJ/cm^2$ and an application time is within a range of 25 to 35 minutes when the application area is intravascular.

8. The operation method according to claim 6, wherein an application energy with a bronchoscopy or a laryngoscopy device is 36 $mJ/cm^2$ and an application duration is within a range of 3 to 6 seconds, when the application area is an intrapulmonary, intratracheal, extracorporeal or oropharyngeal system.

9. The operation method according to claim 6, wherein an application energy with an endoscopy or an colonoscopy device is 36 $mJ/cm^2$ or 120 $mJ/cm^2$, an application duration is within a range of 1 to 60 minutes, when the application area is an intragastric or intragastrointestinal system.

10. The operation method according to claim 9, wherein the application energy is 120 $mJ/cm^2$ and the application duration is within a range of 50 to 60 minutes, when the intragastric or intragastrointestinal system application area is a stomach.

11. The operation method according to claim 9, wherein the application energy is 36 $mJ/cm^2$ and the application duration is within a range of 40 to 44 minutes, when the intragastric or intragastrointestinal system application area is a colon.

12. The operation method according to claim 9, wherein the application energy is 36 $mJ/cm^2$ and the application duration is within a range of 26 to 27 minutes, when the intragastric or intragastrointestinal system application area is a jejunum.

13. The operation method according to claim 9, wherein the application energy is 36 $mJ/cm^2$ and the application duration is within a range of 49 to 50 minutes, when the intragastric or intragastrointestinal system application area is an ileum.

14. The operation method according to claim 9, wherein the application energy is 36 $mJ/cm^2$ and the application duration is within a range of 1 to 2 minutes, when the intragastric or intragastrointestinal system application area is a duodenum.

15. The operation method according to claim 9, wherein the application energy with a cystoscopy device is 36 $mJ/cm^2$ and the application duration is within a range of 2 to 3 minutes, when the intragastric or intragastrointestinal system application area is a bladder.

16. The operation method according to claim 6, wherein an application energy with an arthroscopy device is 36 $mJ/cm^2$ and an application duration is within a range of 3 to 4 minutes, when the application area is an intraarticular system.

17. The operation method according to claim 16, wherein the application area in the intraarticular system is a knee.

18. The operation method according to claim 6, wherein the operation method is used in a treatment of bacterial, fungal, parasitic or viral infections.

19. The operation method according to claim 6, wherein the operation method is used in a treatment of COVID-19 (SARS-CoV-2).

20. The operation method according to claim 19, wherein the operation method is used with antiviral, antimalarial or antibiotic therapy in the treatment of COVID-19 (SARS-CoV-2).

21. A radiation catheter system comprising:
a plurality of radiation sources comprising at least one ultraviolet source selected from UVA, UVB or UVC, at least one red laser LED with a wavelength of 660 nm, at least one blue laser LED with a wavelength of 395 nm and at least one green laser LED with a wavelength of 530 nm,
at least four fiber-optic lines, individually connected to each radiation source of the plurality of radiation sources,
at least one AC/DC power supply, and
an isotonic solution, wherein the isotonic solution enables a transmission of a plurality of radiations.

22. The radiation catheter system according to claim 21, wherein the isotonic solution is a solution containing a plurality of salts providing an isotonic property.

23. The radiation catheter system according to claim 21, further comprising a catheter that has a closed structure such that the isotonic solution remains inside the catheter.

24. The radiation catheter system according to claim 23, wherein the catheter comprises an optical window, wherein the optical window enables the transmission of the plurality of radiations at a closed end.

25. The radiation catheter system according to claim 21, further comprising a catheter that is with or without a camera.

26. The radiation catheter system according to claim 21, further comprising a catheter, wherein a material of the catheter is polyether block amide, polyamide, polyethylene, metal, FEP, PCTFE or Teflon.

27. The radiation catheter system according to claim 21, wherein the radiation catheter system is configured to apply radiation output from at least a portion of the plurality of radiation sources to an intravascular system, an intrapulmonary system, an intrarespiratory system, an intragastric system, an intragastrointestinal system, an intraarticular system, an intravesical system, or an intraurogenital system.

28. An operation method of the radiation catheter system of claim 21, wherein 36 $mJ/cm^2$ or 120 $mJ/cm^2$ energy is applied to an application area with the radiation catheter system.

29. The operation method according to claim 28, wherein an application energy is 36 $mJ/cm^2$ and an application time is within a range of 25 to 35 minutes when the application area is intravascular.

30. The operation method according to claim 28, wherein an application energy with a bronchoscopy or a laryngoscopy device is 36 $mJ/cm^2$ and an application duration is within a range of 3 to 6 seconds, when the application area is an intrapulmonary, intratracheal, extracorporeal or oropharyngeal system.

31. The operation method according to claim 28, wherein an application energy with an endoscopy or colonoscopy device is 36 $mJ/cm^2$ or 120 $mJ/cm^2$, an application duration is within a range of 1 to 60 minutes, when the application area is an intragastric or intragastrointestinal system.

32. The operation method according to claim 31, wherein the application energy is 120 $mJ/cm^2$ and the application duration is within a range of 50 to 60 minutes, when the intragastric or intragastrointestinal system application area is a stomach.

33. The operation method according to claim 31, wherein the application energy is 36 $mJ/cm^2$ and the application duration is within a range of 40 to 44 minutes, when the intragastric or intragastrointestinal system application area is a colon.

34. The operation method according to claim 31, wherein the application energy is 36 mJ/cm$^2$ and the application duration is within a range of 26 to 27 minutes, when the intragastric or intragastrointestinal system application area is a jejunum.

35. The operation method according to claim 31, wherein the application energy is 36 mJ/cm$^2$ and the application duration is within a range of 49 to 50 minutes, when the intragastric or intragastrointestinal system application area is an ileum.

36. The operation method according to claim 31, wherein the application energy is 36 mJ/cm$^2$ and the application duration is within a range of 1 to 2 minutes, when the intragastric or intragastrointestinal system application area is a duodenum.

37. The operation method according to claim 31, wherein the application energy with a cystoscopy device is 36 mJ/cm$^2$ and the application duration is within a range of 2 to 3 minutes, when the intragastric or intragastrointestinal system application area is a bladder.

38. The operation method according to claim 28, wherein an application energy with an arthroscopy device is 36 mJ/cm$^2$ and an application duration is within a range of 3 to 4 minutes, when the application area is an intraarticular system.

39. The operation method according to claim 38, wherein the application area in the intraarticular system is a knee.

40. The operation method according to claim 28, wherein the method is used in a treatment of bacterial, fungal, parasitic, or viral infections.

41. The operation method according to claim 28, wherein the method is used in a treatment COVID-19 (SARS-CoV-2).

42. The operation method according to claim 41, wherein the operation method is used with antiviral, antimalarial, or antibiotic therapy in the treatment of COVID-19 (SARS-CoV-2).

* * * * *